United States Patent [19]
Effland et al.

[11] Patent Number: 5,688,816
[45] Date of Patent: Nov. 18, 1997

[54] CARBAMOYL-1-(PYRIDINYLALKYL)-1H-INDOLES, INDOLINES AND RELATED ANALOGS

[75] Inventors: Richard C. Effland, Bridgewater; Larry Davis, Sergeantsville; Gordon E. Olsen, Somerset, all of N.J.

[73] Assignee: Hoechst Marion Roussel, Inc., Cincinnati, Ohio

[21] Appl. No.: 455,467

[22] Filed: May 31, 1995

Related U.S. Application Data

[62] Division of Ser. No. 248,920, May 25, 1994, Pat. No. 5,455,245, which is a division of Ser. No. 109,526, Aug. 20, 1993, abandoned, which is a division of Ser. No. 835,510, Feb. 14, 1992, Pat. No. 5,264,442, which is a continuation-in-part of Ser. No. 566,724, Aug. 13, 1990, abandoned.

[51] Int. Cl.$^6$ .............. A61K 31/04; C07D 401/14; C07D 405/14; C07D 409/14
[52] U.S. Cl. .............. 514/333; 514/336; 514/343; 546/256; 546/283; 546/284
[58] Field of Search .............. 546/256, 283, 546/284; 514/333, 336, 343

[56] References Cited

U.S. PATENT DOCUMENTS

| | | | |
|---|---|---|---|
| 3,679,692 | 7/1972 | Wu et al. | 546/293 |
| 3,862,953 | 1/1975 | Berger et al. | 546/272 |
| 4,699,907 | 10/1987 | Gasc | 514/232 |
| 4,880,822 | 11/1989 | Effland et al. | 514/339 |
| 5,006,537 | 4/1991 | Effland et al. | 514/399 |
| 5,021,438 | 6/1991 | Junge et al. | 514/373 |
| 5,039,811 | 8/1991 | Effland et al. | 546/273 |
| 5,334,597 | 8/1994 | Prasit | 514/300 |

FOREIGN PATENT DOCUMENTS

| | | |
|---|---|---|
| 0332968 | 9/1989 | European Pat. Off. |
| 2591595 | 6/1987 | France. |
| 2239648 | 2/1973 | Germany. |
| 2102795 | 2/1983 | United Kingdom. |

OTHER PUBLICATIONS

Sheinkman et al. "Synthesis and pharmacology of N-(pyridyalkyl)indoline and indoles" CA 70:19857, 1968.
Wilbraham et al. "Organic and biological chemistry" S.III Univ. pp. 268–269, 1985.
Becker et al. "Mechanisms of cholinesterase inhibition in senile dementia of the alzheimer type" Drug.–Develop. Res. v. 12 163–195, 1988.
A.K. Sheinkman, et al.; Chemical Abstracts 70, 19857b (1969).
T. K. Murray, et al., Psychopharmocology 105, 134 (1991), entitled "Reversal by Tetrahydroaminoacridine of Scopolamine–induced Memory and Performance Deficits in Rats", and published in the United States of America.
National Institute of Mental Health Publication No. ADM 90–1696 (1990), entitled "Useful Information on Alzheimer's Disease" and published in the United States of America.
James F. Flood, et al., Brain Research, 215, 177 (1981) entitled "Cholinergic Receptor Interactions and their Effects on Long–Term Memory Processing"; and published in the Netherlands.
James F. Flood, et al, Psychopharmacology, 86, 61 (1985) entitled "Memory Enhancement: Supra–additive Effect of Subcutaneous Cholinergic Drug Combinations in Mice", and published in the United States of America.
Paul E. Gold, Behavioral and Neural Biology, 46, 87 (1986), entitled "The Use of Avoidance Training in Studies of Modulation of Memory Storage" and published in the United States of America.
Paul E. Gold, Animal Learning & Behavior, 17, 94 (1989), entitled "Neurobiological Features Common to Memory Modulation by Many Treatments", and published in the United States of America.

*Primary Examiner*—Ceila Chang
*Attorney, Agent, or Firm*—Michael J. Sayles

[57] ABSTRACT

This invention relates to compounds of the formula

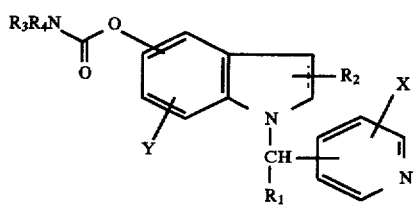

where $R_1$–$R_6$, X and Y are as defined in the specification, which are useful for the treatment of various memory dysfunctions characterized by a cholinergic deficit and thus may be indicated in the treatment of Alzheimer's disease.

1 Claim, No Drawings

CARBAMOYL-1-(PYRIDINYLALKYL)-1H-INDOLES, INDOLINES AND RELATED ANALOGS

This is a division of application Ser. No. 08/248,920 filed May 25, 1994, now U.S. Pat. No. 5,455,245 which is a division of application Ser. No. 08/109,526 filed Aug. 20, 1993, abandoned, which is a division of application Ser. No. 07/835,510 filed Feb. 14, 1992, now U.S. Pat. No. 5,264,442 which is a continuation-in-part of application Ser. No. 07/566,724, filed Aug. 13, 1990, abandoned.

This invention relates to compounds of the formula

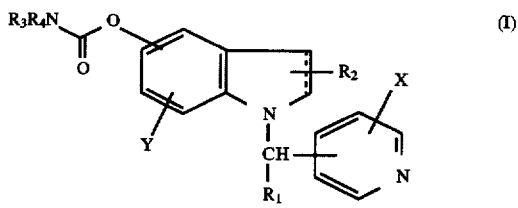

where
- $R_1$ is hydrogen, loweralkyl, arylloweralkyl, loweralkenyl or loweralkynyl;
- $R_2$ is hydrogen, loweralkyl, loweralkenyl, loweralkenyl, formyl or cyano;
- $R_3$ is hydrogen or loweralkyl;
- $R_4$ is loweralkyl, arylloweralkyl, cycloalkyl, aryl, heteroaryl, heteroarylloweralkyl,

or $NR_3R_4$ taken together constitute

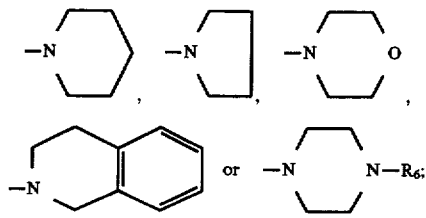

- $R_5$ is hydrogen, loweralkyl or aryl;
- $R_6$ is hydrogen, loweralkyl, aryl, arylloweralkyl, formyl, loweralkanoyl or arylloweralkanoyl,
- X and Y are independently hydrogen, nitro, amino, halogen, loweralkyl, loweralkoxy or hydroxy; or the pharmaceutically acceptable acid addition salts thereof, and where applicable, the geometric and optical isomers and racemic mixtures thereof.

The compounds of this invention are useful for the treatment of various memory dysfunctions characterized by a cholinergic deficit and thus may be indicated in the treatment of Alzheimer's disease.

The dotted lines present in Formula (I) signifies an optional double bond. When the double bond is present, the formula I compounds represent indoles.

Throughout the specification and appended claims, a given chemical formula or name shall encompass all geometrical and optical isomers and racemic mixtures where such isomers and mixtures exist.

Unless otherwise stated or indicated, the following definitions shall apply throughout the specification and the appended claims.

The term "loweralkyl" refers to a straight or branched chain hydrocarbon having from 1 to 6 carbon atoms, e.g., methyl, ethyl, propyl, isopropyl, n-butyl, neopentyl, n-hexyl, etc.

The term "cycloalkyl" refers to a monovalent substituent consisting of a saturated hydrocarbon possessing at least one carbocyclic ring of 3 to 8 carbon atoms, e.g., cyclopropyl, cyclobutyl, cyclopentyl, cyclohexyl, cycloheptyl, etc.

The term "aryl" refers to a phenyl group optionally monosubstituted or disubstituted with a loweralkyl, loweralkoxy, halogen or trifluoromethyl group.

The term "heteroaryl" refers to furanyl, thienyl, pyrrolyl or pyridinyl.

The term "alkanoyl" refers to compounds of the formula

where R is alkyl, e.g., acetyl.

The term "alkenyl" refers to acyclic hydrocarbons with one double bond of the general formula $C_nH_{2n}$, e.g., ethylene, butylene, etc.

The term "alkynyl" refers to acyclic hydrocarbons with one triple bond of the general formula $C_nH_{2n-2}$, e.g. acetylene, butyne, etc.

The term "halogen" refers to a member of the halogen family consisting of fluorine, chlorine, bromine and iodine.

The compounds of this invention are prepared in the following manner. The substituents $R_1$, $R_2$, $R_3$, $R_4$, $R_5$, $R_6$, X and Y are as defined above unless otherwise indicated.

Compound II of the formula

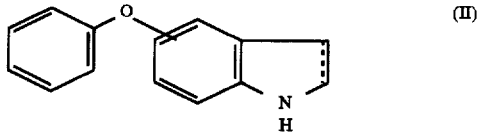

is reacted with a haloalkylpyridine hydrochloride of the formula

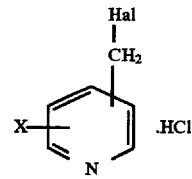

where Hal is halogen, to afford Compound III of the formula

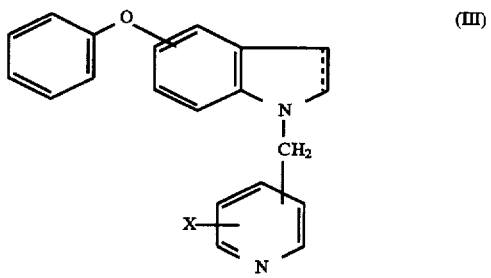

This reaction typically takes place in the presence of a base, such as potassium hydroxide and a solvent such as dimethylsulfoxide or dimethylformamide at ambient temperature for 1 to 20 hours. Compound II is commercially available or can be synthesized from known compounds according to methods known to the art.

Compound III is hydrogenated in a routine manner, for instance, using a noble metal catalyst under a hydrogen atmosphere, to afford Compound IV of the formula

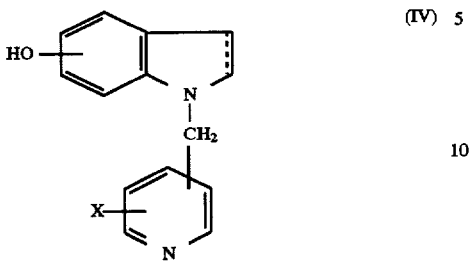
(IV)

The catalyst is selected from palladium or platinum on carbon. The reaction typically takes place at a temperature of about 20° C. to 70° C. for 1 to 20 hours.

Alternatively, to prepare compounds where $R_1 \neq H$, Compound III is reacted with n-butyllithium and a halide of the formula $R_1$-Hal, where $R_1$ is as previously defined and Hal is chlorine or bromine, to afford a compound of the formula

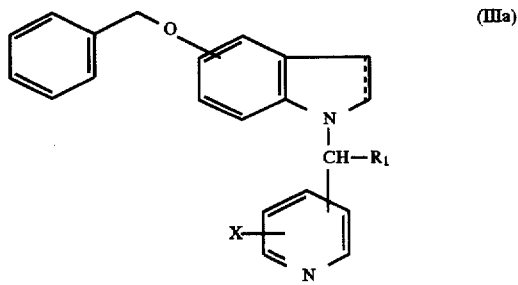
(IIIa)

Typically, this reaction is conducted in tetrahydrofuran or ether at a temperature of −80° to 0° C. for 1 to 6 hours.

Compound IIIa is subsequently hydrogenated in a manner similar to that described above to afford Compound IV where $R_1 \neq$ hydrogen.

Compound IV is allowed to react with an isocyanate of the formula $R_4$—N=C=O in the presence of a base such as potassium carbonate in a suitable solvent such as tetrahydrofuran at a temperature of about 15° C. to 50° C. for 1 to 50 hours to afford compound 1. Alternatively, compound IV is allowed to react with carbonyldiimidazole and an amine of the formula

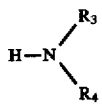

in a routine manner to afford Compound I.

The novel compounds of this invention are useful for the treatment of various memory dysfunctions characterized by a cholinergic deficit, such as that found in Alzheimer's disease and other senile dementia.

This utility is manifested by the ability of these compounds to inhibit the enzyme acetylcholinesterease and thereby increase acetylcholine levels in the brain.

Cholinesterase Inhibition Assay

Cholinesterases are found throughout the body, both in the brain and in serum. However, only brain acetylcholinesterease (AChE) distribution is correlated with central cholinergic innervation. This same innervation is suggested to be weakened in Alzheimer patients. We have determined in vitro inhibition of acetylcholinesterase activity in rat striatum according to the method described below.

In Vitro Inhibition of Acetylcholinesterase Activity in Rat Striatum

Acetylcholinesterase (AChE), which is sometimes called true or specific cholinesterase, is found in nerve cells, skeletal muscle, smooth muscle, various glands and red blood cells. AChE may be distinguished from other cholinesterases by substrate and inhibitor specificities and by regional distribution. Its distribution in the brain correlates with cholinergic innervation and subfractionation shows the highest level in nerve terminals.

It is generally accepted that the physiological role of AChE is the rapid hydrolysis and inactivation of acetylcholine. Inhibitors of AChE show marked cholinomimetic effects in cholinergically-innervated effector organs and have been used therapeutically in the treatment of glaucoma, myasthenia gravis and paralytic ileus. However, recent studies have suggested that AChE inhibitors may also be beneficial in the treatment of Alzheimer's dementia.

The method described below was used in this invention for assaying anticholinesterase activity. This is a modification of the method of Ellman et al., Biochem. Pharmacol. 7, 88 (1961).

Procedure

A. Reagents
1. 0.05M Phosphate buffer, pH 7.2
   (a) 6.85 g $NaH_2PO_4.H_2O$/100 ml distilled $H_2O$
   (b) 13.40 g $Na_2HPO_4.7H_2O$/100 ml distilled $H_2O$
   (c) add (a) to (b) until pH reaches 7.2
   (d) Dilute 1:10
2. Substrate in buffer
   (a) 198 mg acetylthiocholine chloride (10 mM)
   (b) bring to 100 ml with 0.05M phosphate buffer, pH 7.2 (reagent 1)
3. DTNB in buffer
   (a) 19.8 mg 5,5-dithiobisnitrobenzoic acid (DTNB) (0.5 mM)
   (b) bring to 100 ml with 0.05M phosphate buffer, pH 7.2 (reagent 1)
4. A 2 mM stock solution of the test drug is made up in a suitable solvent and bring to volume with 0.5 mM DTNB (reagent 3). Drugs are serially diluted (1:10) such that the final concentration (in cuvette) is $10^{-4}M$ and screened for activity. If active, $IC_{50}$ values are determined from the inhibitory activity of subsequent concentrations.

B. Tissue Preparation

Male Wistar rats are decapitated, brains rapidly removed, corpora striata dissected free, weighed and homogenized in 19 volumes (approximately 7 mg protein/ml) of 0.05M phosphate buffer, pH 7.2, using a Potter-Elvehjem homogenizer. A 25 microliter aliquot of the homogenate is added to 1 ml of vehicle or various concentrations of the test drug and preincubated for 10 minutes at 37° C.

C. Assay

Enzyme activity is measured with the Beckman DU-50 spectrophotometer. This method can be used for $IC_{50}$ determinations and for measuring kinetic constants.

Instrument Settings

Kinetics Soft-Pac Module #598273 (10)

Program #6 Kindata:

Source—Vis
Wavelength—412 nm
Sipper—none
Cuvettes—2 ml cuvettes using auto 6-sampler
Blank—1 for each substrate concentration
Interval time—15 seconds (15 or 30 seconds for kinetics)
Total time—5 minutes (5 or 10 minutes for kinetics)
Plot—yes
Span—autoscale
Slope—increasing
Results—yes (gives slope)
Factor—1

Reagents are added to the blank and sample cuvettes as follows:

Blank: 0.8 ml Phosphate Buffer/DTNB 0.8 ml Buffer/Substrate

Control: 0.8 ml Phosphate Buffer/DTNB/Enzyme 0.8 ml Phosphate Buffer/Substrate

Drug: 0.8 ml Phosphate Buffer/DTNB/Drug/Enzyme 0.8 ml Phosphate Buffer/Substrate Blank values are determined for each run to control non-enzymatic hydrolysis of substrate and these values are automatically substracted by the kindata program available on kinetics soft-pac module. This program also calculates the rate of absorbance change for each cuvette.

For $IC_{50}$ Determinations

Substrate concentration is 10 mM diluted 1:2 in assay yielding final concentration of 5 mM. DTNB concentration is 0.5 mM yielding 0.25 mM final concentration $$\% \text{ Inhibition} = \frac{\text{slope control} - \text{slope drug}}{\text{slope control}} \times 100$$

$IC_{50}$ values are calculated from log-probit analysis. Results of this assay for representative compounds of this invention and physostigmine are presented in Table 1.

TABLE 1

Inhibition of Brain Acetylcholinesterase Activity

| Compound | Inhibitory Concentration $IC_{50}$ (μM) |
| --- | --- |
| 1-(4-pyridinylmethyl)-1H-indol-5-yl methylcarbamate | 6.83 |
| 1-(4-pyridinylmethyl)-1H-indol-5-yl phenylmethylcarbamate | 12.48 |
| Physostigmine (Reference compound) | 0.006 |

This utility is further demonstrated by the ability of these compounds to restore cholinergically deficient memory in the Dark Avoidance Assay described below.

Dark Avoidance Assay

In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment.

Results of this assay for representative compounds of this invention and those for tacrine and pilocarpine (reference compounds) are presented in Table 2.

TABLE 2

| Compound | Dose (mg/kg of body weight, s.c.) | % of Animals with Scopolamine-Induced Memory Deficit Reversal |
| --- | --- | --- |
| 1-[1-(4-pyridinyl-butyl)]-1H-indol-5-yl-methylcarbamate | 1.0 | 20% |
| Tacrine | 0.63 | 13% |

Effective quantities of the compounds of the present invention may be administered to a subject by any one of various methods, for example, orally as in capsules or tablets, parenterally in the form of sterile solutions or suspensions, and in some cases intravenously in the form of sterile solutions. The compounds of the present invention, while effective themselves, may be formulated and administered in the form of their pharmaceutically acceptable addition salts for purposes of stability, convenience of crystallization, increased solubility and the like.

Preferred pharmaceutically acceptable addition salts include salts of inorganic acids such as hydrochloric, hydrobromic, sulfuric, nitric, phosphoric and perchloric acids; as well as organic acids such as tartaric, citric, acetic, succinic, maleic, fumaric, and oxalic acids.

The active compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of compound present in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel™, corn starch and the like; a lubricant such as magnesium stearate or Sterotex®; a gildant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as fatty oil. Other dosage unit forms may contain other various materials which modify the physical form of the doseage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components; a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates phosphates and agents for the adjustment of tonicity such as sodium chloride or dextrose. The parenteral preparation can be enclosed in ampules, disposable syringes or multiple dose vials made of glass or plastic.

Examples of the compounds of the invention are listed below:

1-(4-pyridinylmethyl)-1H-indol-5-yl methylcarbamate;
1-(4-pyridinylmethyl)-1H-indol-5-yl butylcarbamate;
1-(4-pyridinylmethyl)-1H-indol-5-yl phenylmethylcarbamate;
1-[1-(4-pyridinylbutyl)]-1H-indol-5-yl methylcarbamate;
1-[1-(4-pyridinylbutyl)]-1H-indol-5-yl phenylmethylcarbamate;
3-methyl-1-(4-pyridinylmethyl)-1H-indol-5-yl methylcarbamate;
1-[-1-(3-fluoro-4-pyridinyl)butyl]-1H-indol-5-yl ethylcarbamate;
1-[-1-(4-pyridinylbutyl)]-1H-indol-5-yl dimethylcarbamate;
6-fluoro-1-(4-pyridinylmethyl)-1H-indol-5-yl butylcarbamate;
1-[1-(3-fluoro-4-pyridinyl)butyl]-3-methyl-1H-indol-5-yl methylcarbamate;
2,3-dihydro-1-(4-pyridinylmethyl)-1H-indol-5-yl methylcarbamate;
2,3-dihydro-1-[1-(4-pyridinylbutyl)]-1H-indol-5-yl methylcarbamate;
2,3-dihydro-1-[1-(3-fluoro-4-pyridinyl)butyl]-1H-indol-5-yl methylcarbamate;
2,3-dihydro-1-(4-pyridinylmethyl)-1H-indol-5-yl dimethylcarbamate;
1-[1-(4-pyridinylbutyl)]-1H-indol-5-yl 2-phenylcyclopropylcarbamate;
1-[1-(4-pyridinylpropyl)]-1H-indol-5-yl cyclohexylcarbamate;
3-ethyl-1-(3-fluoro-4-pyridinylmethyl)-1H-indol-5-yl (4-phenylmethylpiperazinyl)carbamate;
1-[1-(4-pyridinylbutyl)]-1H-indol-5-yl piperidinylcarbamate;
1-[1-(3-fluoro-4-pyridinylpropyl)]-1H-indol-5-yl morpholinylcarbamate;
2,3-dihydro-1-[1-(4-pyridinylpropyl)]-1H-indol-5-yl cyclohexylcarbamate;
2,3-dihydro-1-[1-(4-pyridinylpropyl)]-1H-indol-5-yl 2-phenylcyclopropylcarbamate;
2,3-dihydro-1-[1-(3-fluoro-4-pyridinylpropyl)]-1H-indol-5-yl piperidinylcarbamate; and
2,3-dihydro-6-fluoro-1-(4-pyridinylbutyl)-1H-indol-5-yl methylcarbamate.

The following examples are for illustrative purposes and are not to be construed as limiting the invention disclosed herein. All temperatures are given in degrees centigrade (° C.) unless indicated otherwise.

EXAMPLE 1

1-(4-Pyridinylmethyl)-1H-indol-5-yl methylcarbamate

To a solution of 1-(4-pyridinylmethyl)-1H-indol-5-ol (2.4 g) in 50 ml tetrahydrofuran, was added milled $K_2CO_3$ (1.5 g), followed by methyl isocyanate (0.65 ml). After stirring at ambient temperature for three hours, the mixture was filtered and the filtrate evaporated to a solid, 3.0 g, m.p. 170° C. This material was eluted on a silica gel column with 2% methanol/dichloromethane via high pressure liquid chromatography (HPLC) and the desired fractions were combined, then evaporated to yield 2.4 g of 1-(4-pyridinylmethyl)-1H-indol-5-yl methylcarbamate, as a solid, m.p. 179°–180° C.

Analysis

Calculated for $C_{16}H_{15}N_3O_2$: 68.31% C 5.38% H 14.94% N

Found: 68.28% C 5.47% H 14.97% N

EXAMPLE 2

1-(4-Pyridinylmethyl)-1H-indol-5-yl butylcarbamate hydrochloride

To a solution of 1-(4-pyridinylmethyl)-1H-indol-5-ol (3.0 g) in 50 ml tetrahydrofuran, was added milled $K_2CO_3$ (1.8 g) followed by butyl isocyanate (1.5 ml). After stirring at ambient temperature for four hours, the mixture was filtered, and the filtrate evaporated to an oil, (~4.5 g) which was eluted on a silica gel column with ethyl acetate/dichloromethane (1:1) via HPLC. The desired fractions were combined and evaporated to yield 3.6 g of a solid, m.p. 135°–137° C. This material was dissolved in methanol, the pH adjusted to 1 with ethereal-HCl and diluted with ether. The resultant precipitate was collected and dried to give 3.0 g of 1-(4-pyridinylmethyl)-1H-indol-5-yl butylcarbamate hydrochloride, m.p. 230° C.(dec).

Analysis

Calculated for $C_{19}H_{21}N_3O_2 \cdot HCl$: 63.41% C 6.16% H 11.68% N

Found: 63.48% C 6.18% H 11.68% N

EXAMPLE 3

1-(4-Pyridinylmethyl)-1H-indol-5-yl phenylmethylcarbamate

To a solution of 1-(4-pyridinylmethyl)-1H-indol-5-ol (2.2 g) in 50 ml tetrahydrofuran, was added milled $K_2CO_3$ (1.4 g) followed by phenylmethyl isocyanate (1.2 ml). After stirring at ambient temperature for twenty hours, the mixture was filtered, and the filtrate evaporated to an oil, (~3.5 g) which was eluted on a silica gel column with ethyl acetate/dichloromethane (1:1) via HPLC. The desired fractions were combined and evaporated to yield 2.8 g of 1-(4-pyridinylmethyl)-1H-indol-5-yl phenylmethylcarbamate, m.p. 112°–114° C.

Analysis

Calculated for $C_{22}H_{19}N_3O_2$: 73.93%C 5.36%H 11.76%N
Found: 73.90%C 5.45%H 11.68%N

EXAMPLE 4

1-[1-(4-Pyridinylbutyl)]-1H-indol-5-yl methylcarbamate

To a solution of 1-[1-(4-pyridinylbutyl)]-1H-indol-5-ol (2.4 g) in 50 ml tetrahydrofuran, was added milled $K_2CO_3$ (1.3 g) followed by methyl isocyanate (0.53 ml). After stirring at ambient temperature for three hours, the mixture was filtered, and the filtrate evaporated to an oil (3.0 g) which was eluted on a silica gel column with ethyl acetate via HPLC. The desired fraction was evaporated to yield 2.2 g of 1-[1-(4-pyridinylbutyl)]-1H-indol-5-yl methylcarbamate, as a solid, m.p. 128°9° C.

Analysis

Calculated for $C_{19}H_{21}N_3O_2$: 70.56%C 6.55%H 12.99%N
Found: 70.31%C 6.42%H 12.87%N

EXAMPLE 5

1-[1-(4-Pyridinylbutyl)]-1H-indol-5-yl p phenylmethylcarbamate

To a solution of 1-[1-(4-pyridinylbutyl)]-1H-indol-5-ol (2.2 g) in 50 ml tetrahydrofuran, was added milled $K_2CO_3$ (1.29 g), followed by phenylmethyl isocyanate (1.0 ml). After stirring at ambient temperature for twenty hours, the mixture was filtered, and the filtrate evaporated to an oil, (3.3 g) which was eluted on a silica gel column with ethyl acetate/dichloromethane (1:1) via HPLC. The desired fraction was evaporated to yield 2.6 g of 1-[1-(4-pyridinylbutyl)]-1H-indol-5-yl phenylmethylcarbamate, as a solid, 119°-21° C.

Analysis

Calculated for $C_{25}H_{25}N_3O_2$: 75.16%C 6.31%H 10.52%N

Found: 75.11%C 6.39%H 10.47%N

We claim:

1. A compound of the formula

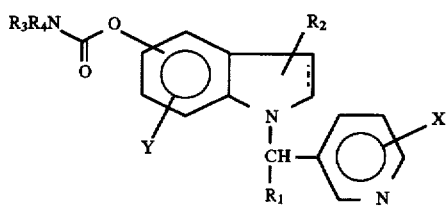

where $R_1$ is hydrogen, loweralkyl, loweralkenyl or loweralkynyl;

$R_2$ is hydrogen, loweralkyl, loweralkenyl, formyl or cyano;

$R_3$ is hydrogen or loweralkyl;

$R_4$ is heteroaryl or heteroarylloweralkyl, wherein the heteroaryl group is selected from the group consisting of furanyl, thienyl, pyrrolyl or pyridinyl;

X and Y are independently hydrogen, nitro, amino, halogen, loweralkyl, loweralkoxy or hydroxy; or the pharmaceutically acceptable acid addition salts thereof, and where applicable, the geometric and optical isomers and racemic mixtures thereof.

* * * * *

UNITED STATES PATENT AND TRADEMARK OFFICE
CERTIFICATE OF CORRECTION

PATENT NO. : 5,688,816

DATED : November 18, 1997

INVENTOR(S) : Richard C. Effland, Larry Davis, Gordon E. Olsen

It is certified that error appears in the above-identified patent and that said Letters Patent is hereby corrected as shown below:

Column 7, Line 25 reads "citrates phosphates" and should read --citrates or phosphates--.

Column 8, Line 1 reads "3-dihydro" and should read --2,3-dihydro--.

Column 9, Line 16 reads "128°9°C" and should read --128-9°C--.

Column 9, Line 23 reads "p phenylmethylcarbamate" and should read --phenylmethylcarbamate--.